United States Patent [19]

Roddy, Sr.

[11] Patent Number: 4,666,408
[45] Date of Patent: May 19, 1987

[54] TABLE SALT COMPARATOR FOR SODIUM RESTRICTED DIETS

[76] Inventor: Charles P. Roddy, Sr., 327 N. Boger Blvd., Lakeland, Fla. 33803

[21] Appl. No.: 812,290

[22] Filed: Dec. 23, 1985

[51] Int. Cl.⁴ ............................................. G09B 19/00
[52] U.S. Cl. .................................................... 434/127
[58] Field of Search ............... 434/127, 276, 298, 365, 434/377, 429, 430, 433, 187, 219

[56] References Cited

U.S. PATENT DOCUMENTS

| | | | |
|---|---|---|---|
| 1,350,237 | 8/1920 | Porter | 434/298 |
| 4,398,721 | 8/1983 | McKay | 434/127 X |
| 4,482,327 | 11/1984 | Brady | 434/219 |

Primary Examiner—William H. Grieb

[57] ABSTRACT

A visual educational device for patients or individuals who want to reduce their dietary sodium intake. It is a series of small clear tubes or vials with different weights of common table salt that are equivalent to various weights of sodium in milligrams per day. These tubes correspond to some of the more typical sodium restricted diets that are in use today. The sealed salt tubes or vials are fixed in holders for viewing and comparing the various sodium restrictions with the average national sodium consumption per day. This device will allow the patient or individual to understand the relationship between the quantity of common table salt consumed per day and the equivalent amount of sodium consumed per day. For very close control of dietary sodium intake this device can be used in conjunction with processed food labeling for sodium content.

1 Claim, 2 Drawing Figures

TABLE SALT COMPARATOR FOR SODIUM RESTRICTED DIETS

BACKGROUND OF INVENTION

This invention relates to a series of common table salt or sodium chloride visual standard indicators equal or equivalent to milligram per day of sodium consumed for patients or individual on various sodium restricted diets that are specified or prescribed in the fields of medicine, nutrition and public health.

BRIEF SUMMARY OF THE INVENTION

The major portion of patients or individuals with hypertension or near hypertension that are placed on sodium restricted diets will probably find it very difficult to visualize the amount of common table salt or sodium chloride equal or equivalent to milligrams per day of sodium specified or prescribed in the restriction. By viewing and comparing the dry salt standard indicators in a comparator form the individual will be able to better comprehend the amount of sodium consumed in milligrams per day for an equivalent weight of table salt or sodium chloride consumed in grams or teaspoons per day, for some of the typical or common sodium restricted diets in use today.

Therefore, it is the principal object of this invention to provide a series of permanent visual standard indicators of salt or sodium chloride mounted in clear glass or plastic vials and tubes, equal or equivalent to milligrams per day of sodium as specified or recommended by the physician for different sodium restricted diets.

A further object of this invention is to provide a series of compact permanent visual standard salt indicators in comparator form to help the patient or individual control his or her sodium consumption during meals and food preparation by being constantly reminded of the relationship between table salt and sodium.

A further object of this invention is to help the patient or individual adhere to the sodium restricted diet.

A further object of this invention is to use it in conjunction with processed food labeling for sodium content.

A further object of this invention is to help educate the estimated 50 million plus hypertension or near hypertension patients or individuals in this country on their sodium consumption or intake.

A further object of this invention is to provide a series of permanent standard table salt indicators in a comparator form that are very economical to produce, compact and refined in appearance.

Still a further object of this invention is to act as a desk top educational tool for physicians when they council or explain to appropriate patients how they can reduce their dietary intake of sodium.

Other objects and advantages of the present invention will become apparent to those skilled in the art as the following description proceeds taken in connection with the accompanying drawing wherein:

BRIEF DESCRIPTION OF EACH OF THE DRAWING FIGURES

DETAILED DESCRIPTION OF THE INVENTION

Figure 1:
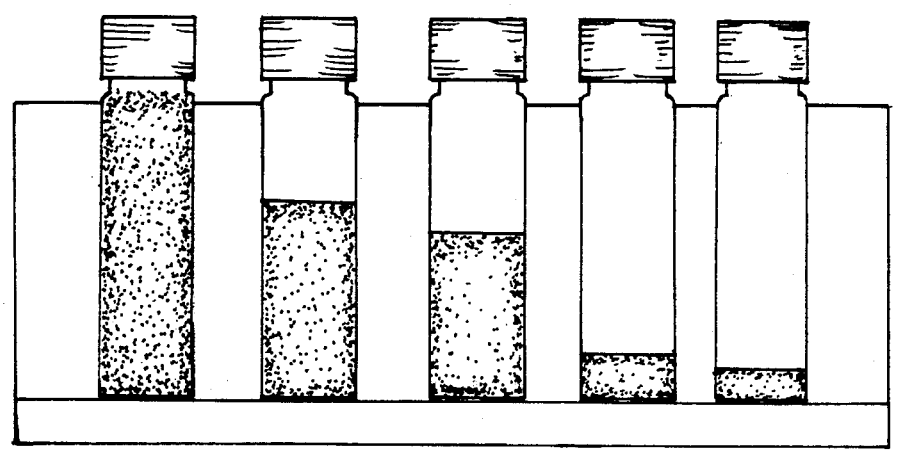
FIG. 1 is a front view of the comparator illustrating five (5) individual common table salt or sodium chloride standard indicators equivalent or equal to milligrams per day sodium for several typical or common sodium restrictions. The tubes or vials are labeled one (1) through five (5) to correspond to the rear view label of weights for table salt and equivalent amounts of sodium.
Figure 2:
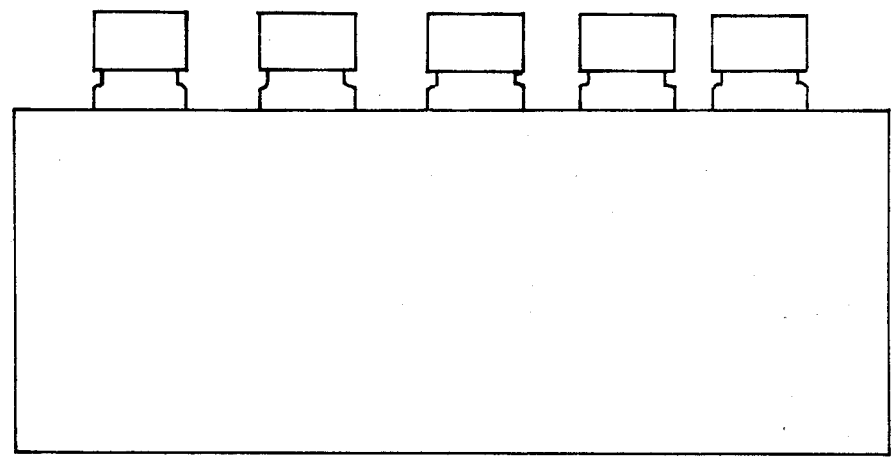
FIG. 2 is a rear view illustrating the label with numbers corresponding to the number on the standard tubes in the front view.

This invention is based on dry weight sodium chloride standard indicators equivalent or equal to milligrams per day of sodium for various sodium restricted diets. The different dry weight standard indicators are calculated from the combining weights of sodium and chlorine in common table salt or sodium chloride, using atomic weight of sodium as 23 and atomic weight of chlorine as 35.5 with a molecular weight of sodium chloride as 58.5. These dry sodium chloride standard indicators are sealed in clear plastic or glass tubes and vials corresponding to a range of sodium restricted diets expressed as milligrams per day. The standard indicators in comparator form for the various sodium restricted diets are compared with the approximate national average sodium consumption as milligrams per day. Each comparator set of visual standard indicators are arranged in series for viewing as shown in FIG. 1. These standards indicate a range of sodium restrictions from 3,000 to 500 milligrams per day as equivalent weight of table salt or sodium chloride. FIG. 2 shows the rear view label with the different weights of sodium chloride and the equivalent weight of sodium for each standard indicator tube. Vial or tube No. 1 indicates the national average sodium consumption of 4800 milligrams per day with the equivalent weight of 12.196 grams or 2.03 teaspoons as table salt or sodium chloride. Vial or tube No. 2 represents a sodium restriction of 3,000 milligrams per day with the equivalent weight of 7.5 grams or 1.25 teaspoons of table salt or sodium chloride. Vial or tube No. 3 represents a common sodium restriction of 2,000 milligrams per day with the equivalent weight of 5.0 grams or 0.833 teaspoons of table salt or sodium chloride. Vial or tube No. 4 represents a sodium restriction of 800 milligrams per day with the equivalent weight of 2.0 grams or 0.33 teaspoons of table salt or sodium chloride. Vial No. 5 represents a sodium restriction of 500 milligrams per day with the equivalent weight of 1.3 grams or 0.216 teaspoon of table salt or sodium chloride.

I claim as my invention:

1. A visual table salt and equivalent sodium comparator for sodium restricted diets in preventative medicine, nutrition and public health, said comparator comprising:

weighed samples of dry common table salt or sodium chloride that are expressed in grams and teaspoons, with each sample being equal or equivalent to milligrams per day of sodium, each dry sample forms a standard and when placed in clear glass or plastic vials and tubes, forms a visual comparator set for viewing the different sodium restrictions, these permanent standards indicate by visual comparison the amount of salt consumed per day for an equivalent or equal amount of sodium consumed per day and ranges from 3,000 to 500 milligrams per day, a label showing the number that corresponds to each standard tube or vial with the following indications, visual dry weight standards of common table salt equal or equivalent to milligrams per day of sodium for various sodium restricted diets, vial or tube 1 shows the national average sodium consumption and indicates 12.196 grams salt per day, equals 2.03 teaspoons, equals 4800 milligrams sodium per day, vial or tube 2 indicates 7.5 grams salt per day, equals 1.25 teaspoons, equals 3,000 milligrams sodium per day, vial or tube 3 indicates 5.0 grams salt per day, equals 0.833 teaspoon, equals 2,000 milligrams sodium per day, vial or tube 4 indicates 2.0 grams salt per day, equals 0.33 teaspoon, equals 800 milligrams sodium per day, vial or tube 5 indicates 1.3 grams salt per day, equals 0.216 teaspoon, equals 500 milligrams sodium per day.

* * * * *